US006815431B2

(12) United States Patent
Tuszynski

(10) Patent No.: US 6,815,431 B2
(45) Date of Patent: Nov. 9, 2004

(54) METHODS FOR THERAPY OF NEURODEGENERATIVE DISEASE OF THE BRAIN

(75) Inventor: Mark H. Tuszynski, La Jolla, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 10/032,952

(22) Filed: Oct. 26, 2001

(65) Prior Publication Data

US 2002/0106350 A1 Aug. 8, 2002

Related U.S. Application Data

(63) Continuation-in-part of application No. 09/620,174, filed on Jul. 19, 2000, now Pat. No. 6,683,058, which is a continuation-in-part of application No. 09/060,543, filed on Apr. 15, 1998, now Pat. No. 6,451,306.

(51) Int. Cl.[7] .................. A01N 43/04; A01N 63/00; C12N 15/00; C12N 15/63; C07H 21/04
(52) U.S. Cl. .................. 514/44; 435/320.1; 435/455; 424/93.2; 424/93.21; 536/23.5
(58) Field of Search .................. 435/320.1, 455; 424/93.2, 93.21; 514/44; 536/23.5

(56) References Cited

U.S. PATENT DOCUMENTS

| | | | |
|---|---|---|---|
| 5,082,670 A | 1/1992 | Gage et al. | 424/520 |
| 5,529,774 A | 6/1996 | Barba et al. | 424/93.21 |
| 5,650,148 A | 7/1997 | Gage et al. | 424/93.2 |
| 5,683,695 A | 11/1997 | Shen et al. | 424/185.1 |
| 5,756,312 A | 5/1998 | Weiner et al. | 435/69.3 |
| 5,762,926 A | 6/1998 | Gage et al. | 424/93.21 |

FOREIGN PATENT DOCUMENTS

WO   WO 90/06757    6/1990

OTHER PUBLICATIONS

Deonarain, M., 1998, Exp. Opin. Ther. Patents, vol. 8, No. 1, p. 53–69.*
Eck et ak., 1996, "Goodman & Gilman's The Pharmacological Basis of therapeutics", Ninth Edition, McGraw–Hill, New York, p. 77–101.*
Gorecki, D., 2001, Expert Opin. Emerging Drugs, vol. 6, No. 2, p. 1870198.*
Castro et al., 2001, Histol. Histopathol., vol. 16, p. 1225–1238.*
Armelin et al., "Pituitary extracts and steroid hormones in the control of 3T3 cell growth" *Proc. Natl. Acad. Sci.* (1973) 70:2702–6.
Banerji et al., "Expression of a beta–globin gene is enhanced by remote SV40 DNA sequences" *Cell* (1981) 27:299–308.
Benoist et al., "In vivo sequence requirements of the SV40 early promoter region" *Nature* (1981) 290:304–10.
Blesch et al., "Ex vivo gene therapy for Alzheimer's disease and spinal cord injury" *Clinical Neuroscience* (1996) 3:268–274.

Borsani et al., "cDNA sequence of human beta–NGF" *Nucleic Acids Res.* (1990) 18:4020.
Breathnach et al., "Organization and expression of eucaryotic split genes coding for proteins" *Ann. Rev. Biochem.* (1981) 50:349–83.
Chen et al., "Calcium phosphate–mediated gene transfer: a highly efficient transfection system for stably transforming cells with plasmid DNA" *BioTechniques* (1988) 6:632–8.
Chen et al., "High–efficiency transformation of mammalian cells by plasmid DNA" *Mol. Cell. Biol.* (1987) 7:2745–52.
Chua et al., "Tumor necrosis factor–alpha induces mRNA for collagenase and TIMP in human skin fibroblasts" *Connect. Tissue Res.* (1990) 25:161–170.
Conner et al., "Distribution of NGF delivered into the rat CNS by either grafted NGF–secreting fibroblasts, intraparenchymal (IP) injections, or IP–infusions" *Society for Neuroscience* (1997) 23:53 Abstract 29.5.
Corden et al., "Promoter sequences of eukaryotic protein–coding genes." *Science* (1980) 209:1406–14.
DePamphilis et al., "Microinjecting DNA into mouse ova to study DNA replication and gene expression and to produce transgenic animals" *BioTechniques* (1988) 6:662–80.
de Wet et al., "The mRNAs for the pro–alpha 1(I) and pro–alpha 2(I) chains of type I procollagen are translated at the same rate in normal human fibroblasts and in fibroblasts from two variants of osteogenesis imperfecta with altered steady state ratios of the two mRNAs" *J. Biol. Chem.* (1983) 258:14385–9.
Elias et al., "Regulation of human lung fibroblast collagen production by recombinant interleukin–1, tumor necrosis factor, and interferon–gamma" *Ann. N.Y. Acad. Sci.* (1990) 580:233–244.
Felgner et al., "Cationic liposome mediated transfection" *Proc. West. Pharmacol. Soc.* (1989) 32:115–21.
Felgner et al., "Cationic liposome mediated transfection" *Focus.* (1989) 11:21–25.
Felgner et al., "Lipofection: a highly efficient, lipid–mediated DNA–transfection procedure" *Proc. Natl. Acad. Sci.* (1987) 84:7413–7.

(List continued on next page.)

*Primary Examiner*—Shin-Lin Chen
(74) *Attorney, Agent, or Firm*—Foley & Lardner, LLP

(57) ABSTRACT

A specific clinical protocol for use toward therapy of defective, diseased and damaged neurons in the mammalian brain, of particular usefulness for treatment of neurodegenerative conditions such as Parkinson's disease and Alzheimer's disease. The protocol is practiced by directly delivering a definite concentration of recombinant neurotrophin, into a targeted region of the brain using an expression vector. The neurotrophin is delivered to, or within close proximity of, identified defective, diseased or damaged brain cells. The method stimulates growth of targeted neurons, and reversal of functional deficits associated with the neurodegenerative disease being treated.

14 Claims, 7 Drawing Sheets

OTHER PUBLICATIONS

Fraley et al., "New generation liposomes: the engineering of an efficient vehicle for intracellular delivery of nucleic acids" *Trends Biochem. Sci.* (1981) 6:77–80.

Fromm et al., "Deletion mapping of DNA regions required for SV40 early region promoter function in vivo" *J. Mol. Appl. Genet.* (1982) 1:457–81.

Gruss et al., "Simian virus 40 tandem repeated sequences as an element of the early promoter" *Proc. Natl. Acad. Sci.* (1981) 78:943–7.

Hefti et al., "Nerve growth factor and Alzheimer's disease" *Ann. Neurol.* (1986) 20:275–81.

Higgins et al., "NGF receptor gene expression is decreased in the nucleus basalis in Alzheimer's disease" *Exp. Neurol.* (1989) 106:222–36.

Horellou et al., "Adenovirus–mediated gene transfer to the central nervous system for Parkinson's Disease" *Experimental Neurobiology* (1997) 144:131–8.

Jolly et al., "Elements in the long terminal repeat of murine retroviruses enhance stable transformation by thymidine kinase gene" *Nucleic Acids Res.* (1983) 11:1855–1872.

Kobayashi et al., "Morphometric study on the CH$ of the nucleus basalis of Meynert in Alzheimer's disease" *Mol. Chem. Neuropathol.* (1991) 15:193–206.

Kojima, et al., "Adenovirus–Mediated transduction with human glial cell line–derived neurotrophic factor gene prevents 1–methyl–4–phenyl–1,2,3,6–tetrahydropyridine–induced dopamine depletion in striatum of mouse brain," *Biochemical and Biophysical Research Communications*, 238:569–573 (1997).

Kordower et al., "The aged monkey basal forebrain: Rescue and sprouting of axotomized basal forebrain neurons after grafts of encapsulated cells secreting human nerve growth factor" *Proc. Natl. Acad. Sci.* (1994) 91:10898–10902.

Lehericy et al., "Heterogeneity and selectivity of the degeneration of cholinergic neurons in the basal forebrain of patients with Alzheimer's disease" *J. Comp. Neurol.* (1993) 330:15–31.

Levivier et al., "Intrastriatal implantation of fibroblasts genetically engineered to produce brain–derived neurotrophic factor prevents degeneration of dopaminergic neurons in a rat model of Parkinson's disease" *The Jo. Of Neuroscience* (1995) 15:7810–20.

Mannino et al., "Liposome mediated gene transfer" *Biotechniques* (1988) 6:682–90.

Maxam et al., "Sequencing end–labeled DNA with base–specific chemical cleavages" *Methods in Enzymology* (1980) 65:499–560.

McCutchan et al., "Enhancement of the infectivity of simian virus 40 deoxy ribonucleic acid with diethylaminoethyldextran" *J. Natl. Cancer Inst.* (1968) 41:351–7.

Messing et al., "A system for shotgun DNA sequencing" *Nucleic Acids Res.* (1981) 9:309–21.

Mesulam et al., "Cholinergic innervation of cortex by the basal forebrain: cytochemistry and cortical connections of the septal area, diagonal band nuclei, nucleus basalis (substantia innominata), and hypothalamus in the rhesus monkey." *J. Comp. Neurol.* (1983) 214:170–197.

Moreau et al., "The SV40 72 base repair repeat has a striking effect on gene expression both in SV40 and other chimeric recombinants" *Nucleic Acids Res.* (1981) 9:6047–6068.

Mufson et al., "Loss of nerve growth factor receptor–containing neurons in Alzheimer's disease: A quantitative analysis across subregions of the basal forebrain" *Exp. Neurol.* (1989) 105:221–32.

Mufson et al., "Nerve growth factor receptor expressing human basal forebrain neurons: pathologic alterations in Alzheimer's and Parkinson's disease" *Prog. Clin. Biol. Res.* (1989) 317:401–14.

Palmer et al., "Genetically modified skin fibroblasts persist long after transplantation but gradually inactivate introduced genes" *Proc. Natl. Acad. Sci.* (1991) 88:1330–4.

Potter et al., "Electroporation in biology: methods, applications, and instrumentation" *Anal. Biochem.* (1988) 174:361–73.

Prockop et al., "Heritable diseases of collagen" *N. Eng. J. Med.* (1984) 311:376–86.

Raymon et al., "Application of ex vivo gene therapy in the treatment of Parkinson's disease" *Experimental Neurobiology* (1997) 144:82–91.

Roberts, et al., "Effects of NGF–Secreting Genetically Modified Cell Grafts on Cholinergic Neuronal Morphology and Cognition in Aged Primates," *Soc. For Neuroscience Abstracts, 21*(2):613.8 (1995).

Rossi et al., "Identification of a cell–specific transcriptional enhancer in the first intron of the mouse alpha 2 (type I) collagen gene" *Proc. Natl. Acad. Sci.* (1987) 84:5590–4.

Schmidt et al., "Regulation of a collagen promoter by the product of viral mos oncogene" *Nature* (1985) 314:286–9.

Seliger et al., "Gamma interferon regulates long terminal repeat–controlled oncogene expression in transformed mouse fibroblasts at the level of mRNA transcription" *J. Virology* (1988) 62:619–21.

Seliger et al., "Tumor necrosis factor–alpha affects LTR–controlled oncogene expression in transformed mouse fibroblasts at the post–transcriptional level" *J. Immunol.* (1988) 141:2138–44.

Shvaloff et al., "Lines of therapeutic research in Alzheimer's disease" *Psychopharmacology Bulletin* (1996) 32:343–52..

Smith et al., "Age–associated neuronal atrophy occurs in the primate brain and is reversible by growth factor gene therapy" *Proc. Natl. Acad. Sci.* (1999) 96:10893–8.

Smith et al., "Characterization of collagen synthesized by normal and chemically transformed rat liver epithelial cell lines" *Biochem.* (1980) 19:1820–5.

Toneguzzo et al., "Electric field–mediated DNA transfer: transient and stable gene expression in human and mouse lymphoid cells" *Molec. Cell. Biol.* (1986) 6:703–6.

Tuszynski et al., "Gene therapy in the adult primate brain: intraparenchymal grafts of cells genetically modified to produce nerve growth factor prevent cholinergic neuronal degeneration" *Gene Therapy* (1996) 3:305–14.

Tuszynski et al., "Recombinant human nerve growth factor infusions prevent cholinergic neuronal degeneration in the adult primate brain" *Ann.. Neurol.* (1991) 30:625–36.

Tuszynski et al., "Somatic gene therapy for nervous system disease" *Ciba Foundation Symposium 196, Growth factors as drugs for neurological and sensory disorder* (1996) 196:85–97.

Tuszynski et al., "Targeted Intraparenchymal Delivery of Human NGF by Gene Transfer to the Primate Basal Forebrain for 3 Months Does Not Accelerate β–Amyloid Plaque Deposition," *Experimental Neurology* (1998) Article No. EN986956 1–10.

Tuszynski et al., "The chronically injured spinal cord exhibits responsiveness to NGF delivered locally by gene therapy" *Society for Neuroscience* (1995) 21:1562 Abstract 613.3.

Ullrich et al., "Human beta–nerve growth factor gene sequence highly homologous to that of a mouse" *Nature* (1983) 303:821–5.

Wolff et al., "Expression of retrovirally transduced genes in primary cultures of rat hepatocytes" *Proc. Natl. Acad. Sci.* (1987) 84:3344–8.

Yang, et al., "Gene Therapy for Central Nervous System Injury: The Use of Cationic Liposomes: An Invited Review," *Journal of Neurotrauma,* 14(5):281–297 (1997).

Zlokovic, et al., "Cellular and Molecular Neurosurgery: Pathways From Concept to Reality—Part II: Vector Systems and Delivery Methodologies for Gene Therapy of The Central Nervous System," *Neurosurgery,* 40(4):805–813 (1997).

Conner, et al., *PNAS USA*, 98:1941–1946 (2001).

von Bartheld, et al., *Mol. Neurobiol.*, 24:1–28 (Humana Press, 2001).

Curtis, et al., *Mol. and Cell. Neurosci.*, 12:105–118 (1998).

von Bartheld, et al., *Letters to Nature*, 379:830–833 (1996).

Sariola and Saarma, *J. Cell Sci.*, 116:3855–3862 (2003).

Ebendal, *J.Neurosci. Rsch.*, 32:461–470 (1992).

\* cited by examiner

METHODS FOR THERAPY OF NEURODEGENERATIVE DISEASE OF THE BRAIN

RELATED U.S. PATENT APPLICATIONS

This is a continuation-in-part of, and claims the priority of, U.S. patent application, Ser. No. 09/620,174 filed on Jul. 19, 2000, now U.S. Pat. No. 6,683,058, which in turns is a continuation in part of Ser. No. 09/060,543, filed on Apr. 15, 1998, now U.S. Pat. No. 6,451,306,

FIELD OF THE INVENTION

The invention relates to methods for treatment of neurodegenerative disease and methods for delivery of therapeutic neurotrophins into the mammalian brain.

HISTORY OF THE RELATED ART

Neurotrophins play a physiological role in the development and regulation of neurons in mammals. In adults, basal forebrain cholinergic neurons, motor neurons and sensory neurons of the CNS retain responsiveness to neurotrophic factors and can regenerate after loss or damage in their presence. For this reason, neurotrophins are considered to have great promise as drugs for the treatment of neurodegenerative conditions such as Alzheimer's Disease (AD), Parkinson's Disease (PD), amyotrophic lateral sclerosis (ALS), peripheral sensory neuropathies and spinal cord injuries.

Direct delivery of neurotrophins through infusion into the neurocompromised brain has been met with limited success and, in one instance, actually worsened the condition being treated (Kordower, et al., Ann. Neurol., 46:419–424, 1999 [symptoms of PD worsened following infusion of glial cell-derived neurotrophic factor]). In contrast, in vivo transduction of CNS cells with a neurotrophin encoding expression vector holds tremendous promise as a more broadly applicable method of treating and preventing neurodegeneration. Ideally, the vector utilized to deliver the neurotrophin will display at least moderate levels of transduction efficiency, while producing minimal toxicity.

SUMMARY OF THE INVENTION

The invention provides a lentiviral-based, clinically useful system and protocol for delivery of recombinant neurotrophins into the mammalian brain. The invention is particularly useful in treating neurodegenerative conditions in primates, in whom neurotrophins delivered according to the invention stimulate growth of neurons and recovery of neurological function.

More specifically, the invention consists of methods for intraparenchymal delivery of neurotrophins to defective, diseased or damaged cells in the mammalian brain using a lentiviral expression vector. In one aspect, the invention provides a specific protocol for use in genetically modifying target neurons ("target cells") to produce a therapeutic neurotrophin; e.g., in the substantia nigra or basal forebrain. The genetic modification of target cells is achieved by in vivo transfection of neurons targeted for treatment, or by transfection of cells neighboring these target neurons (neurons or glia), with a recombinant expression vector for expression of the desired neurotrophin in situ.

The location for delivery of individual unit dosages of neurotrophin into the brain is selected for proximity to previously identified defective, diseased or damaged target cells in the brain. To intensify exposure of such target cells to the endogenous growth factors, each delivery site is situated no more than about 500 $\mu$m from a targeted cell and no more than about 10 mm from another delivery site. The total number of sites chosen for delivery of each unit dosage of neurotrophin will vary with the size of the region to be treated.

Optimally, for delivery of neurotrophin using the lentiviral expression vector, each unit dosage of neurotrophin will comprise 2.5 to 25 $\mu$l of an expression vector composition, wherein the composition includes a viral expression vector in a pharmaceutically acceptable fluid ("neurotrophic composition") and provides from $10^{10}$ up to $10^{15}$ NGF expressing viral particles per ml of neurotrophic composition.

This lentiviral based protocol for neurotrophin delivery achieves a high level of transduction efficiency, with minimal toxicity, to produce a therapeutic or preventative effect in the primate brain.

DETAILED DESCRIPTION OF THE INVENTION

Figure 1:
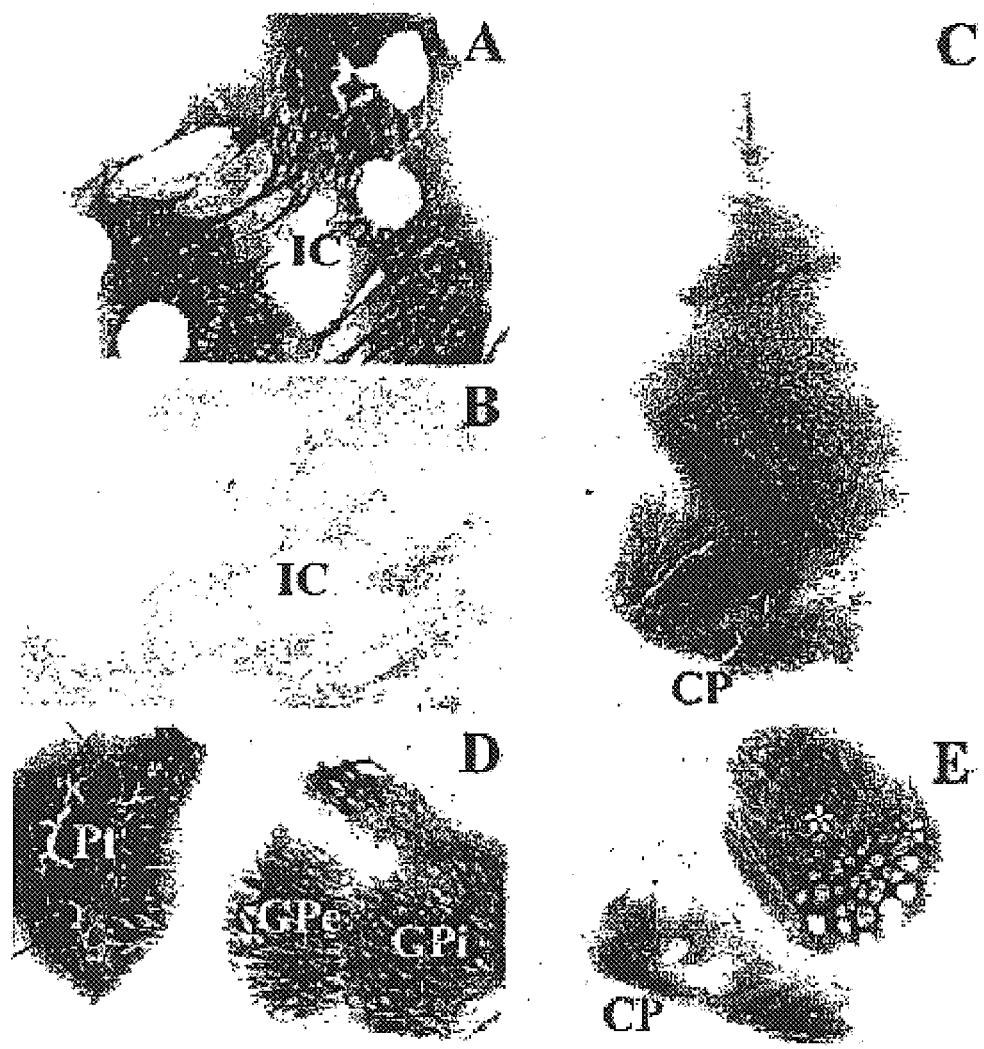
FIG. 1. (A) Dense GDNF immunoreactivity within the head of the caudate nucleus and putamen in a lenti-GDNF-treated aged monkey. (B) In contrast, no GDNF immunoreactivity was observed in these regions in a lenti-Gal-treated animal. IC, internal capsule. (C) Dense GDNF immunoreactivity was observed within the midbrain of a lenti-GDNF-treated animal. (D) GDNF immunoreactivity within the forebrain of a lenti-GDNF-treated monkey. The staining within the putamen (Pt) is from an injection site. The staining within both segments of the globus pallidus (GPe and GPi) is the result of anterograde transport. (E) Anterogradely transported GDNF was also seen in the substantia nigra pars reticulata. Note that the holes in the tissue sections were made post mortem for HPLC analysis. Asterisk in (E) represents a lenti-GDNF injection site (CP, cerebral peduncle). Scale bar in (D) represents 1600 $\mu$m for panels A, B, and D; 1150 $\mu$m for panel C, and 800 $\mu$m for panel E.

I. Target Tissues for Treatment of Neurodegenerative Disorders According to the Invention The invention identifies and defines the required parameters of a method for successful regeneration of neurons in the brain with neurotrophins, especially the neurons whose loss is associated with neurodegenerative conditions with impairment of cognition such as AD.

The first method parameter defined by the invention is selection of a suitable target tissue. A region of the brain is selected for its retained responsiveness to neurotrophic factors. In humans, CNS neurons which retain responsiveness to neurotrophic factors into adulthood include the cholinergic basal forebrain neurons, dopaminergic neurons of the substantia nigra, the entorhinal cortical neurons, the thalamic neurons, the locus coeruleus neurons, the spinal sensory neurons and the spinal motor neurons.

In normal subjects, neurotrophins prevent sympathetic and sensory neuronal death during development and prevents cholinergic neuronal degeneration in adult rats and primates (Tuszynski, et al., Gene Therapy, 3:305–314 (1996)). The resulting loss of functioning neurons in this region of the basal forebrain is believed to be causatively linked to the cognitive decline experienced by subjects suffering from neurodegenerative conditions such as AD. Similarly, loss of functionality in dopaminergic neurons of the substantia nigra is causatively associated with the onset of PD.

Treatment of the targeted region of the brain with vector composition at upwards of 10 separate in vivo gene vector delivery sites is desirable. Importantly, specific gene delivery sites are selected so as to cluster in an area of neuronal loss. Such areas may be identified clinically using a number of known techniques, including magnetic resonance imaging (MRI) and biopsy. In humans, non-invasive, in vivo imaging methods such as MRI will be preferred. Once areas of neuronal loss are identified, delivery sites are selected for stereotaxic distribution so each unit dosage of NGF is delivered into the brain at, or within 500 μm from, a targeted cell, and no more than about 10 mm from another delivery site.

II. Materials for Use in Practicing the Invention

Materials useful in the methods of the invention include in vivo compatible recombinant expression vectors, packaging cell lines, helper cell lines, synthetic in vivo gene therapy vectors, regulatable gene expression systems, encapsulation materials, pharmaceutically acceptable carriers and polynucleotides coding for nervous system growth factors of interest.

A. Neurotrophins

Known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (FGF's 1–15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), and others. NGF and NT-3 in particular have been tested with promising results in clinical trials and animal studies (see, e.g., Hefti and Weiner, Ann Neurol., 20:275–281 (1986); Tuszynki and Gage, Ann. Neurol., 30:625–636 (1991); Tuszynski, et al., Gene Therapy, 3:305–314 (1996) and Blesch and Tuszynski, Clin.Neurosci., 3:268–274 (1996)). Of the known nervous system growth factors, NGF and NT-3 (for treatment of the Ch4 region, as in AD) are preferred for use in the invention.

Human neurotrophins are preferred for use in therapy of human disease according to the invention due to their relatively low immunogenicity as compared to allogenic growth factors. However, other nervous system growth factors are known which may also be suitable for use in the invention with adequate testing of the kind described herein.

Coding polynucleotides for a number of human neurotrophins are known, as are coding sequences for neurotrophins of other mammalian species (e.g., mouse, in which the coding sequence for NGF is highly homologous to the human coding sequence). For example, the coding sequence for hNGF is reported in GenBank at E03015 (Kazuo, et al., Japanese Patent Application No. JP19911175976-A); for GDNF is reported in GenBank at L190262 and L19063; genomic hNGF (with putative amino acid sequence) is reported in GenBank at HSBNGF (Ullrich, Nature, 303:821–825 (1983)); the hNGF mRNA sequence is reported in GenBank at HSBNGFAC (Borsani, et al., Nucleic Acids Res., 18:4020 (1990); and the genomic nucleotide sequence of hNT3 is reported in GenBank at E07844 (Asae, et al., JP Patent Application No. 1993189770-A4). These references are incorporated herein to illustrate knowledge in the art concerning nucleotide and amino acid sequences for use in synthesis of neurotrophins.

B. Recombinant Expression Vectors

The strategy for transferring genes into target cells in vivo includes the following basic steps: (1) selection of an appropriate transgene or transgenes whose expression is correlated with CNS disease or dysfunction; (2) selection and development of suitable and efficient vectors for gene transfer; (3) demonstration that in vivo transduction of target cells and transgene expression occurs stably and efficiently; (4) demonstration that the in vivo gene therapy procedure causes no serious deleterious effects; and (5) demonstration of a desired phenotypic effect in the host animal.

Although other vectors may be used, preferred vectors for use in the methods of the present invention are viral and non-viral vectors. The vector selected should meet the following criteria: 1) the vector must be able to infect targeted cells and thus viral vectors having an appropriate host range must be selected; 2) the transferred gene should be capable of persisting and being expressed in a cell for an extended period of time (without causing cell death) for stable maintenance and expression in the cell; and 3) the vector should do little, if any, damage to target cells.

Because adult mammalian brain cells are non-dividing, the recombinant expression vector chosen must be able to transfect and be expressed in non-dividing cells. At present, vectors known to have this capability include DNA viruses such as adenoviruses, adeno-associated virus (AAV), and certain RNA viruses such as HIV-based lentiviruses, feline immunodeficiency virus (FIV) and equine immunodeficiency virus (EIV. Other vectors with this capability include herpes simplex virus (HSV). However, some of these viruses (e.g., AAV and HSV) can produce toxicity and/or immunogenicity. Recently, an HIV-based lentiviral vector system has recently been developed which, like other retroviruses, can insert a transgene into the nucleus of host cells (enhancing the stability of expression) but, unlike other retroviruses, can make the insertion into the nucleus of non-dividing cells. Lentiviral vectors have been shown to stably transfect brain cells after direct injection, and stably express a foreign transgene without detectable pathogenesis from viral proteins (see, Naldini, et al., Science, 272:263–267 (1996), the disclosure of which is incorporated by reference). Following the teachings of the researchers who first constructed the HIV-1 retroviral vector, those of ordinary skill in the art will be able to construct lentiviral vectors suitable for use in the methods of the invention (for more general reference concerning retrovirus construction, see, e.g., Kriegler, Gene Transfer and Expression, A Laboratory Manual, W. Freeman Co. (NY 1990) and Murray, E J, ed., Methods in Molecular Biology, Vol. 7, Humana Press (NJ 1991)).

Construction of vectors for recombinant expression of nervous system growth factors for use in the invention may be accomplished using conventional techniques which do not require detailed explanation to one of ordinary skill in the art. Specifics for construction of an HIV-1 lentiviral vector are set forth in Example I. For further review, those of ordinary skill may wish to consult Maniatis et al., in Molecular Cloning: A Laboratory Manual, Cold Spring Harbor Laboratory, (NY 1982).

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (Nucleic Acids Res., 9:309, 1981), the method of Maxam, et al., (Methods in Enzymology, 65:499, 1980), or other suitable methods which will be known to those skilled in the art. Size separation of cleaved fragments is performed using conventional gel electrophoresis as described, for example, by Maniatis, et al., (Molecular Cloning, pp. 133–134, 1982).

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)). Methods for maintaining and increasing expression of transgenes in quiescent cells include the use of promoters including collagen type I (1 and 2) (Prockop and Kivirikko, N. Eng. J. Med. 311:376 (1984); Smith and Niles, Biochem. 19:1820 (1980); de Wet et al., J. Biol. Chem., 258:14385 (1983)), SV40 and LTR promoters.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70:2702 (1973)). For example, in the present invention collagen enhancer sequences are used with the collagen promoter 2(I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290:304 (1981), and Fromm and Berg, J. Mol. Appl. Genetics, 1:457 (1982), all of which are incorporated by reference herein. This repeat sequence can increase the transcription of many different viral and cellular genes when it is present in series with various promoters (Moreau et al., Nucleic Acids Res. 9:6047 (1981).

Transgene expression may also be increased for long term stable expression using cytokines to modulate promoter activity. Several cytokines have been reported to modulate the expression of transgene from collagen 2(I) and LTR promoters (Chua et al., connective Tissue Res., 25:161–170 (1990); Elias et al., Annals N.Y. Acad. Sci., 580:233–244 (1990)); Seliger et al., J. Immunol. 141:2138–2144 (1988) and Seliger et al., J. Virology 62:619–621 (1988)). For example, transforming growth factor (TGF), interleukin (IL)-1, and interferon (INF) down regulate the expression of transgenes driven by various promoters such as LTR. Tumor necrosis factor (TNF) and TGF1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll(E)) can also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll(E) promoter-enhancer, and reduces transgene expression.

C. Pharmaceutical Preparations

To form a neurotrophic composition for use in the invention, neurotrophin encoding expression vectors (including, without limitation, viral and non-viral vectors) may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of neurotrophin transgenes may be lyophilized using means well known in the art, for subsequent reconstitution and use according to the invention.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

IV. Methods for Delivery of Vector Composition

Following the protocol defined by the invention, direct delivery of a neurotrophic composition may be achieved by means familiar to those of skill in the art, including microinjection through a surgical incision (see, e.g., Capecchi, Cell, 22:479–488 (1980)); electropotation (see, e.g., Andreason and Evans, Biotechniques, 6:650–660 (1988)); infusion, chemical complexation with a targeting molecule or co-precipitant (e.g., liposome, calcium), and microparticle bombardment of the target tissue (Tang, et al., Nature, 356:152–154 (1992)).

As used in this disclosure, "unit dosage" refers generally to the concentration of neurotrophin/ml of neurotrophic composition. For viral vectors, the neurotrophin concentration is defined by the number of viral particles/ml of neurotrophic composition. Optimally, for delivery of neurotrophin using a viral expression vector, each unit dosage of neurotrophin will comprise 2.5 to 25 µl of a neurotrophic composition, wherein the composition includes a viral expression vector in a pharmaceutically acceptable fluid and provides from $10^{10}$ up to $10^{15}$ expressing viral particles per ml of neurotrophic composition.

The neurotrophic composition is delivered to each delivery cell site in the target tissue by microinjection, infusion, scrape loading, electroporation or other means suitable to directly deliver the composition directly into the delivery site tissue through a surgical sincision. The delivery is accomplished slowly, such as over a period of about 5–10 minutes (depending on the total volume of neurotrophic composition to be delivered).

Those of skill in the art will appreciate that the direct delivery method employed by the invention obviates a limiting risk factor associated with in vivo gene therapy; to wit, the potential for transfection of non-targeted cells with the vector carrying the NGF encoding transgene. In the invention, delivery is direct and the delivery sites are chosen so diffusion of secreted NGF takes place over a controlled and predetermined region of the brain to optimize contact with targeted neurons, while minimizing contact with non-targeted cells.

Startlingly, in primates, viral vectors with an operable neurotrophin encoding transgene have been shown to express human neurotrophin after delivery to the brain and to the CNS for up to 12 months (Example VIII). As such, the invention provides a chronically available source for neurotrophin in the brain.

V. Animal Models and Clinical Evaluation

In non-human primate subjects, the process of aging simulates the neurological changes in the brain experienced in aging humans (Example II). An non-aged animal model that models Parkinson's Disease with a high degree of integrity is 1-methyl-4-phenyl-1,2,3,6-tetrahydropyridine (MPTP) treated monkeys (see, e.g., Kordower, et al., Exp. Neurology, 160:1–16 (1999). Such treatment results in extensive degeneration of dopaminergic neurons in the substantia nigra, with concomitant behavioral modification and motor deficits (Example V). Data demonstrating the use and efficacy of the method of the invention in aged non-human primates is provided in Examples III and IV; and, in MPTP treated animals, in Examples V and VI. The absence of lentiviral immunogenicity in treated animals is confirmed in Example VII.

Clinical evaluation and monitoring of treatment can be performed using the in vivo imaging techniques described above as well as through biopsy and histological analysis of treated tissue. In the latter respect, neuronal numbers can be quantified in a tissue sample with respect to, for example, TH immunoreactivity, anti-neurotrophin antibody (for immunoassay of secreted neurotrophin) or NGF-receptor (p75), and choline acetyltransferase (ChAT) for labeling of neurons. A sample protocol for in vitro histological analysis of treated and control tissue samples is described in the Example II.

The invention having been fully described, examples illustrating its practice are set forth below. These examples should not, however, be considered to limit the scope of the invention, which is defined by the appended claims. Those of ordinary skill in the art will appreciate that while the Examples illustrate an ex vivo application of the invention, the results achieved will be accessible through in vivo delivery of the nervous system growth factor encoding transgenes described, as taught herein, with in vivo gene delivery sites and direct delivery means substituted for the grafting sites and grafting methods discussed in the Examples.

In the examples, the abbreviation "min." refers to minutes, "hrs" and "h" refer to hours, and measurement units (such as "ml") are referred to by standard abbreviations. All printed materials cited are incorporated herein by reference.

EXAMPLE I

Construction of GDNF Expressing Lentiviral Vector

The cDNA coding for a nuclear-localized β-galactosidase (LacZ) and the human GDNF containing a Kozak consensus sequence (a 636-bp fragment: position 1 to 151 and 1 to 485; GenBank accession numbers L19062 and L19063) were cloned in the SIN-W-PGK transfer vector (R. Zufferey, et al., J. Virol. 73, 2886 (1999), incorporated herein by reference). The packaging construct and vesicular stomatis virus G protein (VSV-G) envelope used in this study were the PCMVDR8.92, PRSV-Rev, and the PMD.6 plasmids described previously (see, R. Zufferey, D. Nagy, R. J. Mandel, L. Naldini, D. Trono, Nature Biotechnol. 15, 871 (1997); A. F. Hottinger, M. Azzouz, N. Déglon, P. Gebischer, A. D. Zurn, J. Neurosci. 20, 5587 (2000), incorporated herein by reference). The viral particles were produced in 293T cells as previously described.

The titers (3 to 5×108 TU/ml) of the concentrated LacZ-expressing viruses (200,000 and 250,000 ng p24/ml in experiment 1 and 450,000 ng p24/ml in experiment 2) were determined on 293T cells. The GDNF-expressing viral stocks were normalized for viral particles content using p24 antigen measurement.

EXAMPLE II

Transgene Expression and Anterograde Transport of GDNF Expression Product Within the Aged Primate Brain Non-lesioned aged monkeys that model PD like neuro-degeneration (17) display a slow progressive loss of dopamine within the striatum and tyrosine hydroxylase (TH) within the substantia nigra without frank cellular degeneration. Eight aged (approximately 25 years old) female rhesus monkeys received injections of lentiviral vectors encoding galactosidase (lenti-Gal; n=4) or GDNF (lenti-GDNF; n=4) targeted for the striatum and substantia nigra and were killed 3 months later.

Under MRI guidance, each monkey received six stereotaxic injections of lenti-Gal or lenti-GDNF bilaterally into the caudate nucleus, putamen, and substantia nigra. Injections were made into the head of the caudate nucleus (10 µl), body of the caudate nucleus (5 µl), anterior putamen (10 µl), commissural putamen (10 µl), postcommissural putamen (5 µl), and substantia nigra (5 µl). Injections were made through a 10-µl Hamilton syringe connected to a pump at a rate of 0.5 µl/min.

During the injection, the needle was raised 1 to 2 mm to better disperse the lentivirus through the intended target. The needle was left in place for an additional 3 min to allow the injectate to diffuse from the needle tip. The left side was injected 6 weeks before the right. During the first surgical session, there was a technical failure with the virus aggregating in the needle, which prevented its injection into the brain. This was confirmed at postmortem examination using GDNF-immunohistochemistry and Gal histochemistry. Thus, the left side served as an additional control for the right side. Postmortem, all GDNF injections were localized to the caudate nucleus, putamen, and supranigral regions, as revealed by standard staining procedures.

All aged monkeys receiving lenti-GDNF displayed robust GDNF immunoreactivity within the right striatum (FIG. 1A) and substantia nigra (FIG. 1C). In contrast, no monkeys receiving lenti-Gal displayed specific GDNF immunoreactivity in the right striatum (FIG. 1B). Rather, these monkeys displayed robust expression of Gal similar to that reported previously. In lenti-GDNF-treated animals, GDNF immunoreactivity within the striatum was extremely dense and distributed throughout the neuropil (FIG. 1). When the primary antibody concentration was decreased to one-tenth of the standard, the intense striatal neuropil staining was diminished, and GDNF-immunoreactive perikarya were easily seen. Numerous GDNF-immunoreactive perikarya were also seen within the substantia nigra of lenti-GDNF-injected monkeys.

Within the striatum and substantia nigra, Niss1-stained sections revealed normal striatal cytoarchitecture without significant cytotoxicity. Macrophages were occasionally observed within the needle tracts. Gliosis was similar across treatment groups and was principally confined to the regions immediately surrounding the needle tracts. Lenti-GDNF injections resulted in marked anterograde transport of the trophic factor. Intense GDNF immunoreactivity was observed within fibers of the globus pallidus (FIG. 1D) and substantia nigra pars reticulata (FIG. 1E) after striatal injections. GDNF-containing fibers emanating from putaminal injection sites were seen coursing medially toward and into the globus pallidus (FIG. 1D). These staining patterns were clearly distinct from the injection site and respected the boundaries of the striatal target structures.

In contrast, anterograde transport of Gal was not observed in lenti-Gal monkeys. This suggests that secreted GDNF, and not the virus per se, was anterogradely transported.

EXAMPLE III

DOPA Uptake Following GDNF Treatment in Aged Animals

Aged monkeys underwent fluorodopa (FD) positron emission tomography (PET) before surgery and again just before being killed. Before treatment, all monkeys displayed symmetrical FD uptake in the caudate and putamen bilaterally (ratio: 1.02±0.02) (FIGS. 2A and 2B, left). Similarly, there was symmetrical (4% difference) FD uptake in all lenti-Gal-treated monkeys after lentivirus injections (FIG. 2A, right).

In contrast, FD uptake was significantly asymmetrical (27%) in lenti-GDNF-treated monkeys with greater uptake on the side of the GDNF expression (P<0.007; FIG. 2B, right). With respect to absolute values, lenti-Gal animals displayed a trend toward reduced FD uptake after treatment relative to baseline levels (P=0.06). Qualitatively, three of four lenti-GDNF-treated monkeys displayed clear increases in FD uptake on the treated side.

Within the striatum, lentiviral delivery of GDNF increased a number of markers of dopaminergic function. Optical density measurements were performed to assess the relative intensity of TH staining within the caudate nucleus and putamen (FIGS. 3, A and B).

Figure 3:
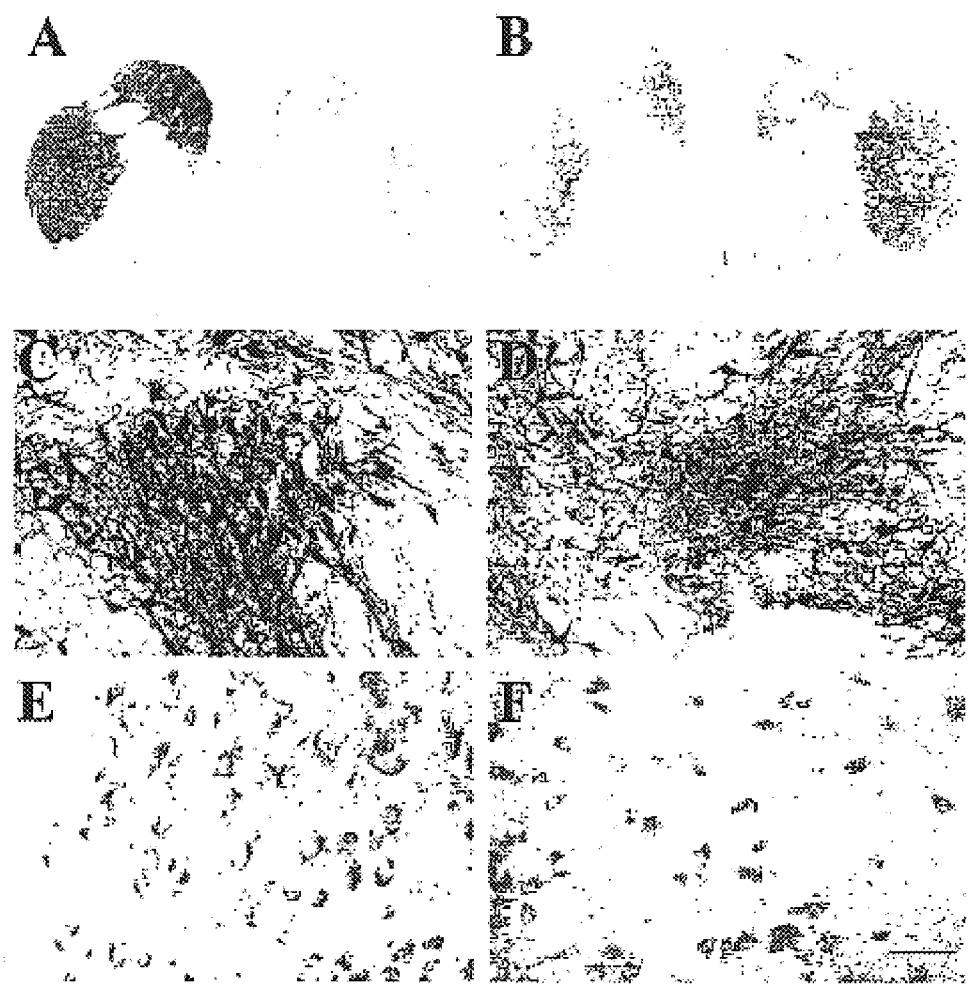
FIG. 3. (A) Section stained for TH immunoreactivity through the anterior commissure illustrating the increase in TH immunoreactivity within the right caudate nucleus and putamen after lenti-GDNF delivery to aged monkeys. (B) Symmetrical and less intense staining for TH immunoreactivity in a monkey injected with lenti-Gal. (C) There were greater numbers and larger TH-immunoreactive neurons within the substantia nigra of a lenti-GDNF-treated animal relative to (D) a lenti-Gal-treated monkey. (E) Lenti-GDNF-treated aged monkeys displayed increased TH mRNA relative to (F) lenti-Gal-treated monkeys in the SN. Scale bar in (F) represents 4500 μm for panels 250 μm for panels (C) and (D) and 100 μm for panels (E) and (F).
Figure 4:
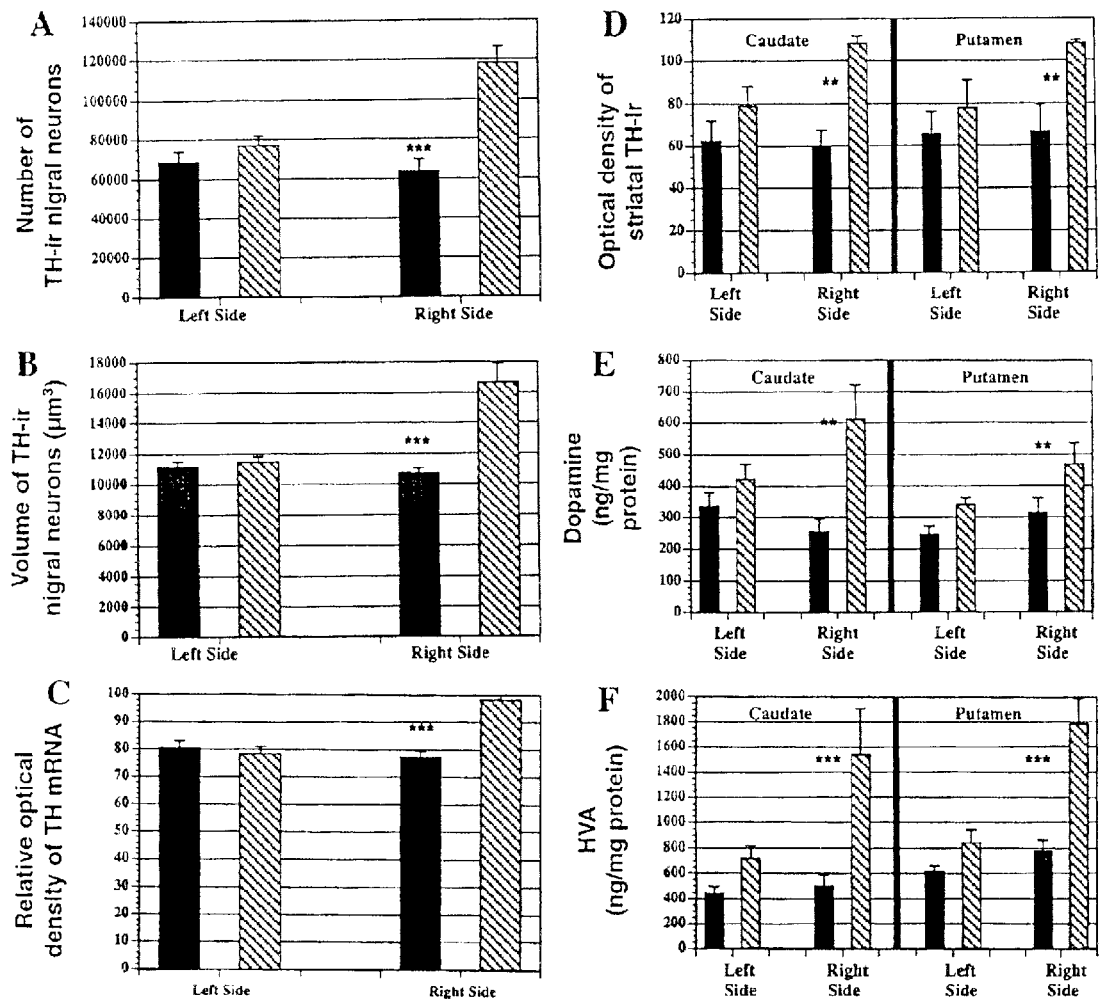
FIG. 4. (A through F) Plots of quantitative data illustrating enhanced nigrostriatal function in lenti-GDNF-treated aged monkeys. Solid bars denote lenti-Gal-treated monkeys; hatched bars indicate lenti-GDNF-treated monkeys. GDNF expression was limited to the right striatum and nigra. P<0.01; *P<0.001.

On the left side where there was no lenti-GDNF expression, the intensity of TH immunoreactivity within the caudate nucleus and putamen was similar between groups (FIGS. 3, A and B). In contrast, significant increases in optical density measures of TH immunoreactivity were seen in the right striatum of lenti-GDNF-infused monkeys (FIG. 3A) relative to lenti-Gal-treated animals (FIG. 3B) or the contralateral side (FIG. 3A). In this regard, there was a 44.1% and a 38.9% increase in optical density measures of TH immunoreactivity within the caudate nucleus and putamen, respectively (FIG. 4D). At the time of death, tissue punches were taken throughout the caudate nucleus and putamen of all monkeys. Relative to lenti-Gal-treated animals, measurement of dopamine (DA) and homovanillic acid (HVA) revealed significant increases in the right caudate nucleus (140% DA, P<0.001; 207% HVA, P<0.001) and putamen (47.2% DA, P<0.05; 128% HVA, P<0.01) in lenti-GDNF-treated aged monkeys (FIG. 4, E and F).

EXAMPLE IV

Neuron Generation in Aged Animals

Lentiviral delivery of GDNF to aged monkeys resulted in an increase in the number of TH-immunoreactive neurons within the substantia nigra (FIGS. 3, C and D). Regardless of the extent of GDNF immunoreactivity within the midbrain, the organization of TH-immunoreactive neurons was similar in all animals, and these neurons were not observed in ectopic locations within this locus.

Stereological counts revealed an 85% increase in the number of TH-immunoreactive nigral neurons on the side receiving lentivirally delivered GDNF (FIG. 4A) relative to lenti-Gal-treated animals. On the side (left) that did not display GDNF immunoreactivity, lenti-GDNF-treated animals contained 76,929±4918 TH-immunoreactive neurons. This is similar to what was seen in lenti-Gal-infused animals (68,543±5519). Whereas lenti-Gal-infused monkeys contained 63,738±6094 TH-immunoreactive nigral neurons in the right side, lenti-GDNF-treated monkeys contained 118,170±8631 TH-immunoreactive nigral neurons in this hemisphere (P<0.001).

A similar pattern was seen when the volume of TH-immunoreactive substantia nigra neurons was quantified (FIG. 4B). TH-immunoreactive neurons from lenti-Gal- and lenti-GDNF-treated monkeys were similar in size in the left nigra where there was no GDNF expression (11,147.5±351 $\mu$m3 and 11,458.7±379 $\mu$m3, respectively). In contrast, a 35% increase in neuronal volume was seen on the GDNF-rich right side in lenti-GDNF-injected aged monkeys (lenti-Gal 10,707.5±333 $\mu$m3; lenti-GDNF 16,653.7±1240 $\mu$m3; P<0.001).

Although stereological counts of TH mRNA-containing neurons were not performed, there was an obvious increase in the number of TH mRNA-containing neurons within the right substantia nigra in lenti-GDNF-treated monkeys (FIG. 3E) compared with lenti-Gal-containing animals (FIG. 3F). With regard to the relative levels of TH mRNA expression within individual nigral neurons, the pattern of results was similar to that observed with TH-immunoreactive neuronal number and volume (FIG. 4C). On the left side, the optical density of TH mRNA within nigral neurons was similar between lenti-Gal- and lenti-GDNF-treated monkeys (78.28±2.78 and 80.58±2.5, respectively). In contrast, there was a significant (21.5%) increase in the optical density for TH mRNA in lenti-GDNF-treated monkeys (98.3±1.5) relative to lenti-Gal-treated monkeys (77.2±2.3) on the right side (P<0.01).

EXAMPLE V

Functional Recovery in Chemically Impaired Animals

For a second model of neurodegenerative changes similar to those occurring in PD, young adult monkeys received unilateral intracarotid injections of 1-methyl-4-phenyl-1,2,3,6-tetrahydropyridine (MPTP) to induce extensive nigrostriatal degeneration, resulting in a behavioral syndrome characterized by robust motor deficits.

In the second experiment, 20 young adult rhesus were initially trained 3 days per week until asymptotic performance was achieved on a hand-reach task in which the time to pick up food treats out of recessed wells was measured (16, 24). Each experimental day, monkeys received 10 trials per hand. Once per week, monkeys were also evaluated on a modified parkinsonian clinical rating scale (CRS). All monkeys then received an injection of 3 mg MPTP-HCl into the right carotid artery, initiating a parkinsonian state.

One week later, monkeys were evaluated on the CRS. Only monkeys displaying severe hemiparkinsonism with the classic crooked arm posture and dragging leg on the left side continued in the study (n=10). Monkeys with this behavioral phenotype generally display the most severe lesions neuroanatomically and do not display spontaneous recovery behaviorally.

On the basis of CRS scores, monkeys were matched into two groups of five monkeys, which received on that day lenti-Gal or lenti-GDNF treatment. Using magnetic resonance imaging (MRI) guidance, all monkeys were given lentivirus injections into the caudate nucleus (n=2), putamen (n=3), and substantia nigra (n=1) on the right side using the same injection parameters as in experiment 1. One week later, monkeys began retesting on the hand-reach task three times per week for 3 weeks per month.

For statistical analyses, the times for an individual week were combined into a single score. During the weeks of hand-reach testing, monkeys were also scored once per week on the CRS. Individuals blinded to the experimental treatment performed all behavioral assessments.

Figure 5:
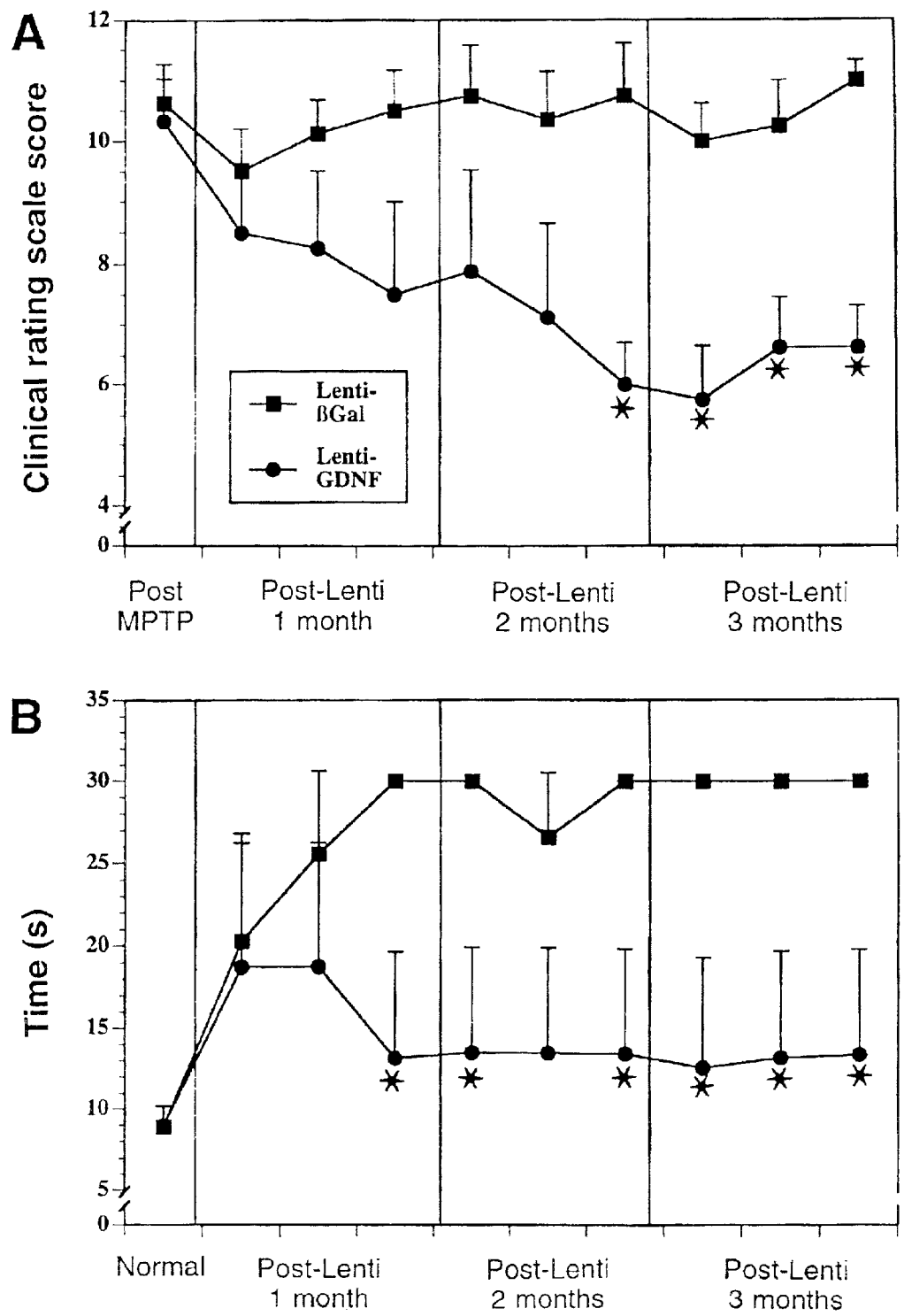
FIG. 5. After MPTP-treatment, lenti-GDNF-injected monkeys displayed functional improvement on (A) the clinical rating scale and (B) the hand-reach task. All tests were performed 3 weeks per month [see (15)]. On the clinical rating scale, monkeys were matched into groups based upon the post-MPTP score. For the hand-reach task, each symbol represents the mean of three sessions per week for the left hand. Monkeys were not tested on this task during the week between MPTP and lentivirus injection. *P<0.05 relative to lenti-Gal.

Before MPTP treatment, all young adult monkeys scored 0 on the CRS. After MPTP, but before lentivirus injection, monkeys in the lenti-GDNF and lenti-Gal groups averaged 10.4±0.07 and 10.6±0.6, respectively, on the CRS (P>0.05). After lentivirus treatment, significant differences in CRS scores were seen between the two groups (Kolmogorov-Smirnov test, P<0.0001; FIG. 5A). CRS scores of monkeys receiving lenti-Gal did not change over the 3-month period after treatment. In contrast, CRS scores of monkeys receiving lenti-GDNF significantly diminished during the 3-month period after treatment. Scores began to decrease in the first month after lenti-GDNF treatment. However, statistically significant differences between lenti-GDNF and lenti-Gal were only discerned at posttreatment observations 6, 7, 8, and 9 (Kolmogorov-Smirnov test, P <0.04 for each comparison).

Lenti-GDNF-treated animals also improved performance on the operant hand-reach task. Under the conditions before MPTP administration, animals in both groups performed this task with similar speed (FIG. 5B). For the "unaffected" right hand, no differences in motor function were discerned for either group relative to performance before MPTP administration or to each other (P>0.05). In contrast, performance with the left hand was significantly improved in lenti-GDNF-treated animals relative to controls (P<0.05).

After MPTP, all lenti-Gal-treated animals were severely impaired, with monkeys often not performing at all, or requiring more than the maximally allowed 30 s. In contrast, three of the four lenti-GDNF monkeys performed the task with the left hand at near-normal levels, whereas one lenti-GDNF-treated monkey was impaired and performed this task in a manner similar to the lenti-Gal-treated animals. Between groups, significant differences in performance were discerned on posttreatment tests 4, 6, 7, 8, and 9 (P<0.05 for each comparison).

EXAMPLE VI

Neuron Generation in Chemically Impaired Animals

Figure 2:
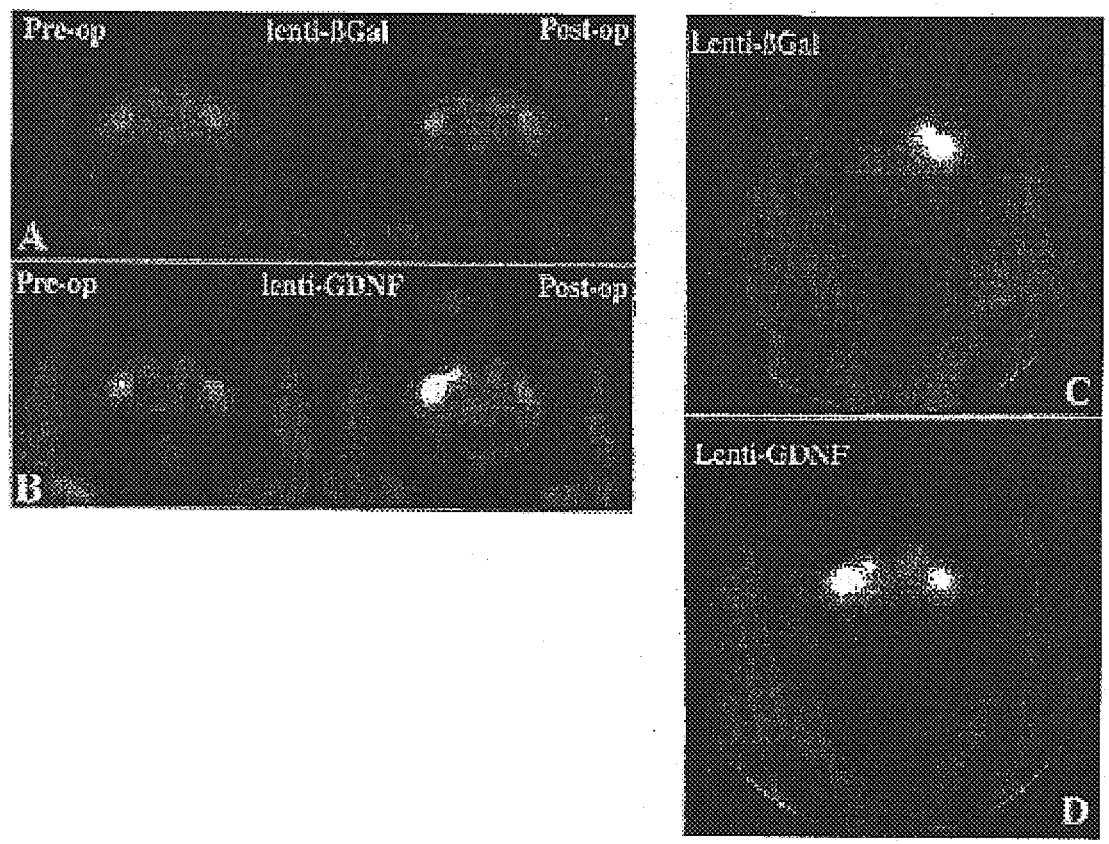
FIG. 2. PET scan data evaluating the influence of lenti-GDNF on FD uptake in (A and B) intact aged monkeys and (C and D) young adult MPTP-treated monkeys. (A) FD uptake did not change from baseline to 3 months after lentivirus injection in lenti-Gal-treated aged monkeys. (B) In contrast, lenti-GDNF injections manifested increased FD uptake on the side of GDNF expression relative to preoperative levels in aged monkeys. Ki values (per minute) for the striatum are as follows: (left side) lenti-Gal preoperative 0.0068±0.0001, lenti-Gal postoperative 0.0062±0.0002; (right side) lenti-Gal preoperative 0.0068±0.0002, lenti-Gal postoperative 0.0065±0.0001; (left side) lenti-GDNF preoperative 0.0072±0.0005, lenti-GDNF postoperative 0.0068±0.0003; (right side) lenti-GDNF preoperative 0.0076±0.0004, lenti-GDNF postoperative 0.0081±0.0003. (C) After MPTP lesions, a comprehensive loss of FD uptake was seen within the right striatum of lenti-Gal-treated young adult monkeys. (D) In contrast, FD uptake was enhanced in lenti-GDNF-treated monkeys. Ki values (per minute) for the striatum are as follows: lenti-Gal left, 0.0091±0.0004; lenti-Gal right, 0.0017±0.0005; lenti-GDNF left, 0.0084±0.0004; lenti-GDNF right, 0.0056±0.0018.

All monkeys underwent FD PET scans. Qualitatively, all lenti-Gal-treated monkeys displayed pronounced FD uptake in the left striatum and a comprehensive loss of FD uptake on the right side (FIG. 2C). In contrast, two of four lenti-GDNF-treated animals displayed robust and symmetrical FD uptake on both sides (FIG. 2D). The remaining two lenti-GDNF monkeys displayed reduced FD uptake on the right side, but with Ki values 50 to 100% greater than lenti-Gal controls (FIG. 2). Quantitatively, no differences in FD uptake were observed between groups within the left striatum (P>0.05). In contrast, there was a significant (>300%) increase in FD uptake in lenti-GDNF-treated animals in the right striatum relative to lenti-Gal-treated animals (P<0.05). When the right striatum was subdivided, significant increases in FD uptake were only seen within the putamen of lenti-GDNF-treated animals (P<0.05).

After death, a strong GDNF-immunoreactive signal was seen in the caudate nucleus, putamen, and substantia nigra of all lenti-GDNF-treated, but none of the lenti-Gal-treated animals. The intensity and distribution of GDNF immunoreactivity was indistinguishable from what was observed in aged monkeys (see FIG. 1).

Figure 6:
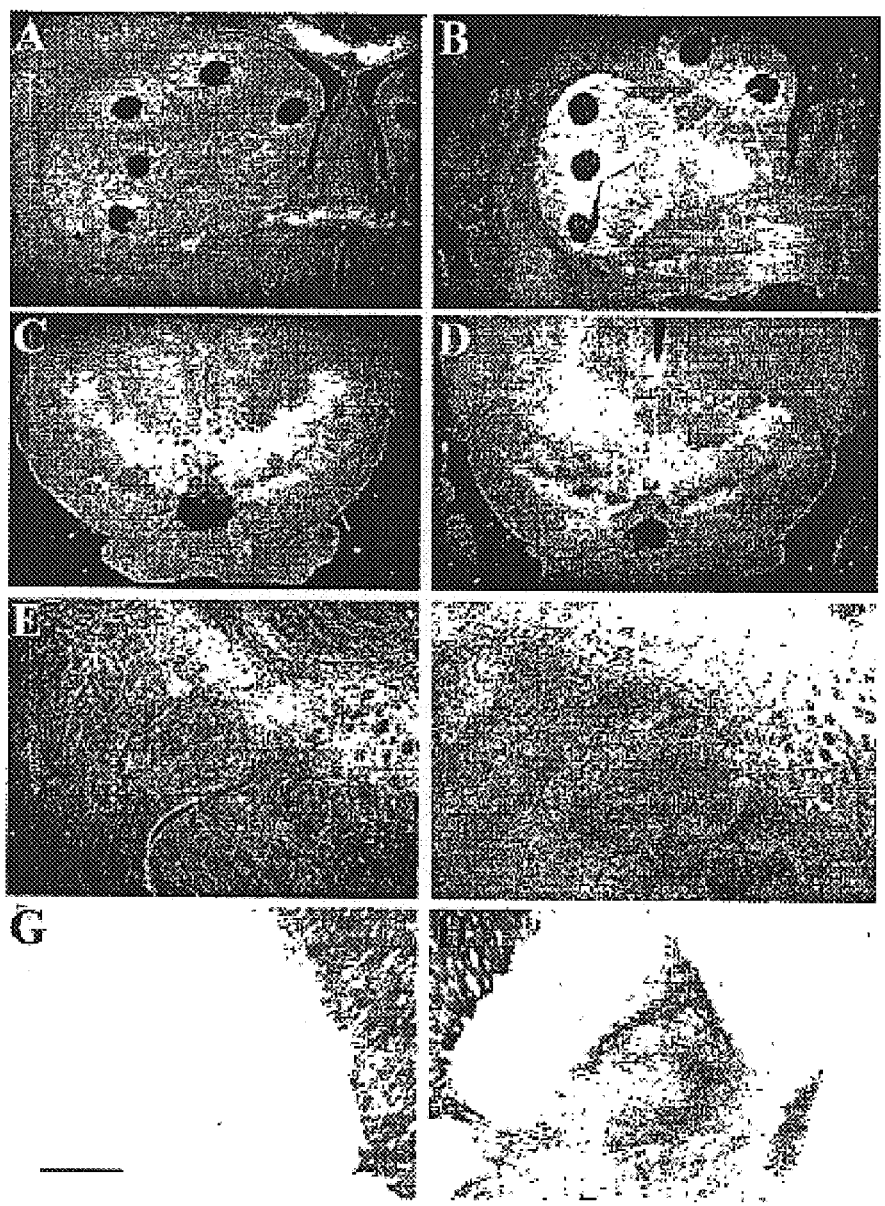
FIG. 6. (A and B) Low-power dark-field photomicrographs through the right striatum of TH-immunostained sections of MPTP-treated monkeys treated with (A) lenti-Gal or (B) lenti-GDNF. (A) There was a comprehensive loss of TH immunoreactivity in the caudate and putamen of lenti-Gal-treated animal. In contrast, near normal level of TH immunoreactivity is seen in lenti-GDNF-treated animals. Low-power (C and D) and medium-power (E and F) photomicrographs of TH-immunostained section through the substantia nigra of animals treated with lenti-Gal (C and E) and lenti-GDNF (D and F). Note the loss of TH-immunoreactive neurons in the lenti-Gal-treated animals on the side of the MPTP-injection. TH-immunoreactive sprouting fibers, as well as a supranormal number of TH-immunoreactive nigral perikarya are seen in lenti-GDNF-treated animals on the side of the MPTP injection. (G and H) Bright-field low-power photomicrographs of a TH-immunostained section from a lenti-GDNF-treated monkey. (G) Note the normal TH-immunoreactive fiber density through the globus pallidus on the intact side that was not treated with lenti-GDNF. (H) In contrast, an enhanced network of TH-immunoreactive fibers is seen on the side treated with both MPTP and lenti-GDNF. Scale bar in (G) represents the following magnifications: (A), (B), (C), and (D) at 3500 μm; (E), (F), (G), and (H) at 1150 μm.

All lenti-Gal-treated monkeys displayed a comprehensive loss of TH immunoreactivity within the striatum on the side ipsilateral to the MPTP injection (FIG. 6A). In contrast, all lenti-GDNF-treated monkeys displayed enhanced striatal TH immunoreactivity relative to Gal controls (FIG. 6B).

There was variability in the degree of striatal TH immunoreactivity in lenti-GDNF-treated animals and that variability was associated with the degree of functional recovery seen on the hand-reach task. Two lenti-GDNF-treated monkeys displayed dense TH immunoreactivity throughout the rostrocaudal extent of the striatum (FIG. 6B). In these monkeys, the intensity of the TH immunoreactivity was greater than that observed on the intact side. These two animals displayed the best functional recovery.

A third lenti-GDNF-treated monkey also displayed robust functional recovery on the hand-reach task. However, the enhanced striatal TH immunoreactivity in this animal was limited to the post-commissural putamen. The fourth lenti-GDNF-treated monkey did not recover on the hand-reach task. Although putaminal TH immunoreactivity in this animal was still greater than controls, the degree of innervation was sparse and restricted to the medial post-commissural putamen.

Figure 7:
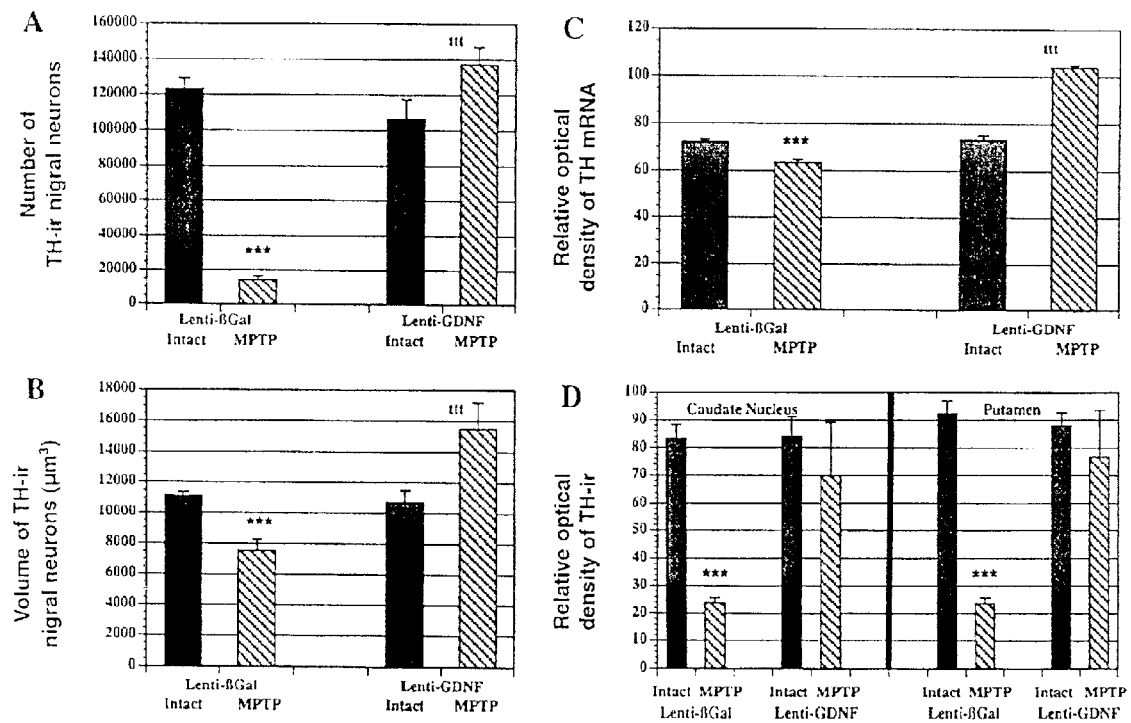
FIG. 7. (A through D) Quantification of lenti-GDNF's trophic effects on nigral neuronal number, volume, TH mRNA and striatal TH immunoreactivity in MPTP-treated monkeys. ***P<0.001 significant decreases relative to intact side; ttt denotes significant increases relative to the intact side.

Lenti-GDNF treatment enhanced the expression of TH-immunoreactive fibers throughout the nigrostriatal pathway. Unlike what was observed in aged monkeys, however, some TH-immunoreactive fibers in the striatum displayed a morphology characteristic of both degenerating and regenerating fibers. Large, thickened fibers could be seen coursing in an irregular fashion in these animals. Rostrally, these fibers appeared disorganized at times, with a more normal organization seen more caudally. TH-immunoreactive sprouting was also seen in the globus pallidus (FIGS. 6, G and H), substantia innominata (FIGS. 6, A and B), and lateral septum. These novel staining patterns were not immunoreactive for dopamine-hydroxylase confirming the dopaminergic phenotype of this response. Quantitatively, lenti-Gal-treated monkeys displayed significant decreases in the optical density of TH-immunoreactive fibers within the right caudate nucleus (71.5%; P<0.006; FIG. 7D) and putamen (74.3% P<0.0007; FIG. 7D) relative to the intact side. When analyzed as a group, TH optical density in the right caudate nucleus and putamen of lenti-GDNF-treated monkeys was significantly greater than that seen in lenti-Gal-treated monkeys (P<0.001 for both) and was similar to that seen on the intact side of these animals (P>0.05 for both).

All lenti-Gal-treated monkeys displayed a dramatic loss of TH-immunoreactive neurons within the substantia nigra on the side ipsilateral to the MPTP injection (FIG. 7A). In contrast, the nigra from all four of the lenti-GDNF-treated displayed complete neuroprotection (FIG. 7A), regardless of the degree of functional recovery. In lenti-Gal-treated monkeys, intracarotid injections of MPTP resulted in an 89% decrease in the number (FIG. 7A), and an 81.6% decrease in the density, of TH-immunoreactive nigral neurons on the side ipsilateral to the toxin injection (P<0.001).

In contrast, lenti-GDNF-treated monkeys displayed 32% more TH-immunoreactive nigral neurons (P<0.001) and an 11% increase in TH-immunoreactive neuronal density (P<0.05) relative to the intact side. In lenti-Gal-treated animals, MPTP significantly reduced (32%) the volume of residual TH-immunoreactive nigral neurons on the lesion side relative to the intact side (P<0.001; FIG. 7B). The volume of TH-immunoreactive neurons in lenti-GDNF-treated animals was significantly larger (44.3%) on the lesioned side relative to the intact side (P<0.001).

Finally, the optical density of TH mRNA was quantified bilaterally in all animals (FIG. 7C). In lenti-Gal-treated animals, there was a significant decrease (24.0%) in the relative optical density of TH mRNA within residual neurons on the MPTP-lesioned side relative to the intact side (P<0.03). In contrast, lenti-GDNF-treated animals displayed a significant increase (41.7%) in relative optical density of TH mRNA relative to the intact side or lenti-Gal-treated animals (P<0.001).

EXAMPLE VII

Absence of Lentiviral Immunoreactivity in Treated Animals

Sections from all monkeys were stained for CD45, CD3, and CD8 markers to assess the immune response after lentiviral vector injection. These antibodies are markers for activated microglia, T cells, and leukocytes including lymphocytes, monocytes, granulocytes, eosinophils, and thymocytes. Staining for these immune markers was weak, and often absent, in these animals. Mild staining for CD45 and CD8 was seen in two animals. Some CD45-immunoreactive cells displayed a microglial morphology. Other monkeys displayed virtually no immunoreactivity even in sections containing needle tracts.

EXAMPLE VIII

Long Term GDNF Expression in Treated Animals

Two additional intact young adult rhesus monkeys received lenti-GDNF injections into the right caudate and putamen and the left substantia nigra using the same injection protocol utilized in Example VI. These animals were killed 8 months later and were evaluated by immunohistochemistry and enzyme-linked immunosorbent assay (ELISA) for long-term gene expression.

Robust GDNF immunoreactivity was seen in the right caudate, right putamen, and left ventral midbrain in both animals. In the right substantia nigra, many GDNF-immunoreactive neurons were seen. This labeling represents retrograde transport of GDNF after injections of lenti-GDNF into the right striatum. Further, dense GDNF-immunoreactive fiber staining, representing anterograde transport of the trophic factor, was seen within the right substantia nigra pars reticulata. Tissue punches taken at the time of death revealed significant levels of GDNF produced by striatal cells 8 months after lenti-GDNF injections.

On the side without a striatal injection, $0.130 \pm 0.062$ and $0.131 \pm 0.060$ ng/mg protein of GDNF were seen in the caudate nucleus and putamen, respectively. Significantly higher GDNF levels were observed within the caudate nucleus ($2.25 \pm 0.312$ ng/mg protein; P<0.001) and putamen ($3.5 \pm 0.582$ ng/mg protein; P<0.001) on the lenti-GDNF-injected side.

The invention claimed is:

1. A method for delivery of a therapeutic neurotrophin to targeted defective, diseased or damaged dopaminergic neurons in the mammalian brain, the method comprising directly delivering a neurotrophic composition, comprising a neurotrophin encoding expression vector, into one or more delivery sites within a region of the brain containing targeted neurons, whereby the neurotrophin is expressed in, or within 500 μm from, a targeted cell, and no more than about 10 mm from another delivery site; and wherein further contact with the neurotrophin ameliorates the defect, disease or damage.

2. The method according to claim 1, wherein the region of the brain containing the targeted neurons is the substantia nigra.

3. The method according to claim 2, wherein the treated mammal is a human who is suffering from Parkinson's disease, and the disease is ameliorated by stimulation of growth of dopaminergic neurons.

4. The method according to claim 3, wherein the disease is ameliorated by reversal of deficits in motor function associated with the Parkinson's disease.

5. The method according to claim 1, wherein the expression vector is a lentiviral expression vector.

6. The method according to claim 5, wherein the lentiviral expression vector is HIV-1.

7. The method according to claim 1, wherein the treated mammal is a human and the expression vector encodes a human neurotrophin.

8. The method according to claim 7, wherein the neurotrophin is human glial cell-derived neurotrophic factor (GDNF).

9. The method according to claim 1, wherein the neurotrophin is neurturin.

10. The method according to claim 1, wherein the neurotrophin is NGF.

11. The method according to claim 1, wherein the neurotrophin is NT-4/5.

12. The method according to claim 1, wherein the neurotrophin is persephin.

13. The method according to claim 1, wherein from 2.5 μl to 25 μl of the composition is delivered to each delivery site.

14. The method according to claim 1, wherein the expression vector is an adeno-associated vector.

* * * * *